(12) United States Patent
Tso et al.

(10) Patent No.: US 9,051,394 B2
(45) Date of Patent: Jun. 9, 2015

(54) APOLIPOPROTEIN AIV AS AN ANTIDIABETIC PEPTIDE

(75) Inventors: Patrick Tso, Cincinnati, OH (US); Sean Davidson, Cincinnati, OH (US); Stephen Woods, Cincinnati, OH (US); Fei Wang, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 13/980,749

(22) PCT Filed: Jan. 19, 2012

(86) PCT No.: PCT/US2012/021802
§ 371 (c)(1),
(2), (4) Date: Sep. 17, 2013

(87) PCT Pub. No.: WO2012/100010
PCT Pub. Date: Jul. 26, 2012

(65) Prior Publication Data
US 2014/0005107 A1    Jan. 2, 2014

Related U.S. Application Data

(60) Provisional application No. 61/434,196, filed on Jan. 19, 2011.

(51) Int. Cl.
| | |
|---|---|
| A61K 38/00 | (2006.01) |
| A61P 3/08 | (2006.01) |
| A61P 3/10 | (2006.01) |
| A61K 38/28 | (2006.01) |
| A61P 7/12 | (2006.01) |
| A61K 38/14 | (2006.01) |
| A61K 38/16 | (2006.01) |
| A01N 43/04 | (2006.01) |
| A61K 31/70 | (2006.01) |
| C07K 9/00 | (2006.01) |
| C07K 5/00 | (2006.01) |
| C07K 7/00 | (2006.01) |
| C07K 16/00 | (2006.01) |
| C07K 17/00 | (2006.01) |
| C07K 14/775 | (2006.01) |
| A61K 38/22 | (2006.01) |
| A61K 39/00 | (2006.01) |
| C07K 14/47 | (2006.01) |
| A61K 38/17 | (2006.01) |
| C07K 14/655 | (2006.01) |
| C07K 14/605 | (2006.01) |
| A61K 38/26 | (2006.01) |

(52) U.S. Cl.
CPC ............... *C07K 14/775* (2013.01); *A61K 38/00* (2013.01); *A61K 38/28* (2013.01); *A61K 38/22* (2013.01); *A61K 39/00* (2013.01); *C07K 14/47* (2013.01); *A61K 38/177* (2013.01); *C07K 14/6555* (2013.01); *C07K 14/605* (2013.01); *C07K 9/008* (2013.01); *A61K 38/26* (2013.01); *C07K 9/005* (2013.01); *A61K 38/1709* (2013.01)

(58) Field of Classification Search
None
See application file for complete search history.

(56) References Cited

U.S. PATENT DOCUMENTS

2010/0267052 A1 * 10/2010 Gelber et al. .................. 435/7.1

FOREIGN PATENT DOCUMENTS

| CN | 1668645 A | 9/2005 | | |
|---|---|---|---|---|
| WO | WO-93/15198 A1 | 8/1993 | | |
| WO | WO 9315198 A1 * | 8/1993 | ............. | C12N 15/12 |
| WO | WO-94/27629 A1 | 12/1994 | | |
| WO | WO 03097696 A1 * | 11/2003 | ............. | C07K 16/00 |
| WO | WO-2009/116861 A2 | 9/2009 | | |
| WO | 2010060387 A1 | 6/2010 | | |

OTHER PUBLICATIONS

Elshourbagy et al., "The Nucleotide and Amino Acid Sequence of Human Apolipoprotein A-IV mRNA and the Close Linkage of Its Gene to the Genes of Apolipoproteins A-I and C-III," J. Biol. Chem. 261:1998-2002 (1986).*
Mahley et al., "Plasma Lipoproteins: apolipoprotein and function," J. Lipid Res. 25:1277-1294 (1984).*
Database Biosis, [Online] (2002), "Physiology of the small intestine in the glycemic control and the treatment of diabetes mellitus".
Fujimoto, K. et al., "Suppression of Food Intake by Apoliproprotein A-IV is Mediated through the Central Nervous System in Rats," J. Clin. Invest., 9:1830-1833 (1993).
Glatzle J, et al., Apolipoprotein A-IV stimulates duodenal vagal afferent activity to inhibit gastric motility via a CCK1 pathway, Am J Physiol Regul Integr Comp Physiol. 2004;287(2):R354-9.
International Search Report and Written Opinion issued in PCT/US2012/021802.
Okumura T, et al., Apolipoprotein A-IV acts in the brain to inhibit gastric emptying in the rat, Am J Physiol. 1996; 270(1 Pt 1):G49-53.
Okumura T, et al: "Physiology of the small intestine in the glycemic control and the treatment of diabetes mellitus", Folia Pharmacologica Japonica, 120(1), 2002, pp. 29-31.
Suen, et al: "The potential of incretin-based therapies in type 1 diabetes", Drug Discovery Today, vol. 17. No. 1, (2012), pp. 89-95.
Van Belle, et al: "Type 1 diabetes: etiology, immunology, and therapeutic strategies", Physiological Reviews 91(1), 2011, pp. 79-118.
NCBI Database; Accession No. P06727.3; GI: 93163358, Mar. 7, 2006.

* cited by examiner

*Primary Examiner* — James H Alstrum Acevedo
*Assistant Examiner* — Thea D'Ambrosio
(74) *Attorney, Agent, or Firm* — McCarter & English, LLP; Steven G. Davis; Mei Bai

(57) ABSTRACT

Methods for treating type two diabetes mellitus in a subject in need thereof and pharmaceutical compositions for the treatment of type two diabetes mellitus are disclosed. The methods include administering an effective amount of apolipoprotein A-IV to the subject. The pharmaceutical composition includes apolipoprotein A-IV formulated for administration to a subject for the treatment of type two diabetes mellitus. Also disclosed are methods for substantially restoring glucose tolerance in a subject in need thereof to a normal level and methods for lowering blood glucose levels in a subject in need thereof.

22 Claims, 19 Drawing Sheets

IPGTT in female WT and AIV-KO mice human islets treated with human A-IV

When the human islets were depolarized by 30mM KCl plus 250μM Dz, 10μg/ml hA-IV showed a significantly stimulatory effect on insulin secretion.

EVSADQVATVMWDYFSQLSNNAKEAVEHLQKSELTQQLNALFQDKLGEVNTY
AGDLQKKLVPFATELHERLAKDSEKLKEEIGKELEELRARLLPHANEVSQKIGD
NLRELQQRLEPYADQLRTQVNTQAEQLRRQLTPYAQRMERVLRENADSLQAS
LRPHADELKAKIDQNVEELKGRLTPYADEFKVKIDQTVEELRRSLAPYAQDTQE
KLNHQLEGLTFQMKKNAEELKARISASAEELRQRLAPLAEDVRGNLRGNTEGL
QKSLAELGGHLDQQVEEFRRRVEPYGENFNKALVQQMEQLRQKLGPHAGDV
EGHLSFLEKDLRDKVNSFFSTFKEKESQDKTL*S*LPELEQQQEQQQEQQQEQV
QMLAPLES

SEQ ID NO. 1

FIG. 15

EVTSDQVANVVWDYFTQLSNNAKEAVEQFQKTDVQQLST
LFASTYADGVHNKLVPFVVQLSGHLAQETERVKEEIKKEL
EDLRDRKTQTFGENMQKLQEHLKPYAVDLQDQINTQTQE
MKLQLTPYIQRMQTTIKENVDNLHTSMMPLATNLKDKFN
RNMEELKGHLTPRANELKATIDQNLEDLRRSLAPLTVGVQ
EKLNHQMEGLAFQMKKNAEELQTKVSAKIDQLQKNLAPL
VEDVQSKVKGNTEGLQKSLEDLNRQLEQQVEEFRRTVEP
MGEMFNKALVQQLEQFRQQLGPNSGEVESHLSFLEKSLRE
KVNSFMSTLEKKGSPDQPQALPLPEQAQEQAQEQAQEQVQ
PKPLES

SEQ ID NO. 2

FIG. 16

GEVSADQVATVMWDYFSQLSNNAKEAVEHLQKSELTQQLNALFQDKL
GEVNTYAGDLQKKLVPFATELHERLAKDSEKLKEEIGKELEELRARLLPHANEV
SQKIGDNLRELQQRLEPYADQLRTQVNTQAEQLRRQLTPYAQRMERVLRENA
DSLQASLRPHADELKAKIDQNVEELKGRLTPYADEFKVKIDQTVEELRRSLAPY
AQDTQEKLNHQLEGLTFQMKKNAEELKARISASAEELRQRLAPLAEDVRGNLR
GNTEGLQKSLAELGGHLDQQVEEFRRRVEPYGENFNKALVQQMEQLRQKLG
PHAGDVEGHLSFLEKDLRDKVNSFFSTFKEKESQDKTLSLPELEQQQEQQQE
QQQEQVQMLAPLES

SEQ ID NO. 3

FIG. 17

X₁EVSADQVATVMWDYFSQLSNNAKEAVEHLQKSELTQQLNALFQDKL
GEVNTYAGDLQKKLVPFATELHERLAKDSEKLKEEIGKELEELRARLLPHANEV
SQKIGDNLRELQQRLEPYADQLRTQVNTQAEQLRRQLTPYAQRMERVLRENA
DSLQASLRPHADX₂LKAKIDQNVEELKGRLTPYADEFKVKIDQTVEELRRSLAP
YAQDTQEKLNHQLEGLTFQMKKNAEELKARISASAEELRQRLAPLAEDVRGNL
RGNTEGLQKSLAELGGHLDQQVEEFRRRVEPYGENFNKALVQQMEQLRQKL
GPHAGDVEGHLSFLEKDLRDKVNSFFSTFKEKESQDKX₃LSLPELEQQQEQX₃
QEQQQEQVQMLAPLES

X₁ is G, A, V or absent

X₂ is E or K

X₃ is T or S

X₄ is Q or H

SEQ ID NO. 4

FIG. 18

```
GTCAGTGCTGACCAGGTGGCCACAGTGATGTGGGACTACTTCAGCC
AGCTGAGCAACAATGCCAAGGAGGCCGTGGAACATCTCCAGAAATCTGAA
CTCACCCAGCAACTCAATGCCCTCTTCCAGGACAAACTTGGAGAAGTGAAC
ACTTACGCAGGTGACCTGCAGAAGAAGCTGGTGCCCTTTGCCACCGAGCT
GCATGAACGCCTGGCCAAGGACTCGGAGAAACTGAAGGAGGAGATTGGGA
AGGAGCTGGAGGAGCTGAGGGCCCGGCTGCTGCCCCATGCCAATGAGGT
GAGCCAGAAGATCGGGGACAACCTGCGAGAGCTTCAGCAGCGCCTGGAG
CCCTACGCGGACCAGCTGCGCACCCAGGTCAACACGCAGGCCGAGCAGC
TGCGGCGCCAGCTGACCCCCTACGCACAGCGCATGGAGAGAGTGCTGCG
GGAGAACGCCGACAGCCTGCAGGCCTCGCTGAGGCCCCACGCCGACGAG
CTCAAGGCCAAGATCGACCAGAACGTGGAGGAGCTCAAGGGACGCCTTAC
GCCCTACGCTGACGAATTCAAAGTCAAGATTGACCAGACCGTGGAGGAGC
TGCGCCGCAGCCTGGCTCCCTATGCTCAGGACACGCAGGAGAAGCTCAAC
CACCAGCTTGAGGGCCTGACCTTCCAGATGAAGAAGAACGCCGAGGAGCT
CAAGGCCAGGATCTCGGCCAGTGCCGAGGAGCTGCGGCAGAGGCTGGCG
CCCTTGGCCGAGGACGTGCGTGGCAACCTGAGGGGCAACACCGAGGGGC
TGCAGAAGTCACTGGCAGAGCTGGGTGGGCACCTGGACCAGCAGGTGGA
GGAGTTCCGACGCCGGGTGGAGCCCTACGGGGAAAACTTCAACAAAGCCC
TGGTGCAGCAGATGGAACAGCTCAGGCAGAAACTGGGCCCCCATGCGGG
GGACGTGGAAGGCCACCTGAGCTTCCTGGAGAAGGACCTGAGGGACAAG
GTCAACTCCTTCTTCAGCACCTTCAAGGAGAAAGAGAGCCAGGACAAGACT
CTCTCCCTCCCTGAGCTCGAGCAACAGCAGGAACAGCAGCAGGAGCAGCA
GCAGGAGCAGGTGCAGATGCTGGCCCCTTTGGAGAGC
```

SEQ ID NO. 5

FIG. 19

SEQUENCE LISTING

```
<160> NUMBER OF SEQ ID NOS: 5

<210> SEQ ID NO 1
<211> LENGTH: 376
<212> TYPE: PRT
<213> ORGANISM: Homo sapiens

<400> SEQUENCE: 1

Glu Val Ser Ala Asp Gln Val Ala Thr Val Met Trp Asp Tyr Phe Ser
1               5                   10                  15

Gln Leu Ser Asn Asn Ala Lys Glu Ala Val Glu His Leu Gln Lys Ser
            20                  25                  30

Glu Leu Thr Gln Gln Leu Asn Ala Leu Phe Gln Asp Lys Leu Gly Glu
        35                  40                  45

Val Asn Thr Tyr Ala Gly Asp Leu Gln Lys Lys Leu Val Pro Phe Ala
    50                  55                  60

Thr Glu Leu His Glu Arg Leu Ala Lys Asp Ser Glu Lys Leu Lys Glu
65                  70                  75                  80

Glu Ile Gly Lys Glu Leu Glu Glu Leu Arg Ala Arg Leu Leu Pro His
                85                  90                  95

Ala Asn Glu Val Ser Gln Lys Ile Gly Asp Asn Leu Arg Glu Leu Gln
            100                 105                 110

Gln Arg Leu Glu Pro Tyr Ala Asp Gln Leu Arg Thr Gln Val Asn Thr
        115                 120                 125

Gln Ala Glu Gln Leu Arg Arg Gln Leu Thr Pro Tyr Ala Gln Arg Met
    130                 135                 140

Glu Arg Val Leu Arg Glu Asn Ala Asp Ser Leu Gln Ala Ser Leu Arg
145                 150                 155                 160

Pro His Ala Asp Glu Leu Lys Ala Lys Ile Asp Gln Asn Val Glu Glu
                165                 170                 175

Leu Lys Gly Arg Leu Thr Pro Tyr Ala Asp Glu Phe Lys Val Lys Ile
            180                 185                 190

Asp Gln Thr Val Glu Glu Leu Arg Arg Ser Leu Ala Pro Tyr Ala Gln
        195                 200                 205

Asp Thr Gln Glu Lys Leu Asn His Gln Leu Glu Gly Leu Thr Phe Gln
    210                 215                 220

Met Lys Lys Asn Ala Glu Glu Leu Lys Ala Arg Ile Ser Ala Ser Ala
225                 230                 235                 240

Glu Glu Leu Arg Gln Arg Leu Ala Pro Leu Ala Glu Asp Val Arg Gly
                245                 250                 255
```

```
Asn Leu Arg Gly Asn Thr Glu Gly Leu Gln Lys Ser Leu Ala Glu Leu
            260                 265                 270

Gly Gly His Leu Asp Gln Gln Val Glu Glu Phe Arg Arg Val Glu
        275                 280                 285

Pro Tyr Gly Glu Asn Phe Asn Lys Ala Leu Val Gln Gln Met Glu Gln
        290                 295                 300

Leu Arg Gln Lys Leu Gly Pro His Ala Gly Asp Val Glu Gly His Leu
305                 310                 315                 320

Ser Phe Leu Glu Lys Asp Leu Arg Asp Lys Val Asn Ser Phe Phe Ser
                325                 330                 335

Thr Phe Lys Glu Lys Glu Ser Gln Asp Lys Thr Leu Ser Leu Pro Glu
            340                 345                 350

Leu Glu Gln Gln Glu Gln Gln Glu Gln Gln Gln Glu Gln Val
                355                 360                 365

Gln Met Leu Ala Pro Leu Glu Ser
        370                 375

<210> SEQ ID NO 2
<211> LENGTH: 361
<212> TYPE: PRT
<213> ORGANISM: Mus musculus

<400> SEQUENCE: 2

Glu Val Thr Ser Asp Gln Val Ala Asn Val Val Trp Asp Tyr Phe Thr
1               5                   10                  15

Gln Leu Ser Asn Asn Ala Lys Glu Ala Val Glu Gln Phe Gln Lys Thr
            20                  25                  30

Asp Val Gln Gln Leu Ser Thr Leu Phe Ala Ser Thr Tyr Ala Asp Gly
        35                  40                  45

Val His Asn Lys Leu Val Pro Phe Val Val Gln Leu Ser Gly His Leu
    50                  55                  60

Ala Gln Glu Thr Glu Arg Val Lys Glu Val Ile Lys Lys Glu Leu Glu
65                  70                  75                  80

Asp Leu Arg Asp Arg Lys Thr Gln Thr Phe Gly Glu Asn Met Gln Lys
                85                  90                  95

Leu Gln Glu His Leu Lys Pro Tyr Ala Val Asp Leu Gln Asp Gln Ile
            100                 105                 110

Asn Thr Gln Thr Gln Glu Met Lys Leu Gln Leu Thr Pro Tyr Ile Gln
        115                 120                 125

Arg Met Gln Thr Thr Ile Lys Glu Asn Val Asp Asn Leu His Thr Ser
    130                 135                 140

Met Met Pro Leu Ala Thr Asn Leu Lys Asp Lys Phe Asn Arg Asn Met
145                 150                 155                 160

Glu Glu Leu Lys Gly His Leu Thr Pro Arg Ala Asn Glu Leu Lys Ala
                165                 170                 175

Thr Ile Asp Gln Asn Leu Glu Asp Leu Arg Arg Ser Leu Ala Pro Leu
            180                 185                 190

Thr Val Gly Val Gln Glu Lys Leu Asn His Gln Met Glu Gly Leu Ala
        195                 200                 205

Phe Gln Met Lys Lys Asn Ala Glu Glu Leu Gln Thr Lys Val Ser Ala
    210                 215                 220

Lys Ile Asp Gln Leu Gln Lys Asn Leu Ala Pro Leu Val Glu Asp Val
225                 230                 235                 240

Gln Ser Lys Val Lys Gly Asn Thr Glu Gly Leu Gln Lys Ser Leu Glu
```

```
                    245                 250                 255
Asp Leu Asn Arg Gln Leu Glu Gln Gln Val Glu Glu Phe Arg Arg Thr
                260                 265                 270

Val Glu Pro Met Gly Glu Met Phe Asn Lys Ala Leu Val Gln Gln Leu
            275                 280                 285

Glu Gln Phe Arg Gln Gln Leu Gly Pro Asn Ser Glu Val Glu Ser
        290                 295                 300

His Leu Ser Phe Leu Glu Lys Ser Leu Arg Glu Lys Val Asn Ser Phe
305                 310                 315                 320

Met Ser Thr Leu Glu Lys Lys Gly Ser Pro Asp Gln Pro Gln Ala Leu
                325                 330                 335

Pro Leu Pro Glu Gln Ala Gln Glu Gln Ala Gln Glu Gln Ala Gln Glu
            340                 345                 350

Gln Val Gln Pro Lys Pro Leu Glu Ser
        355                 360

<210> SEQ ID NO 3
<211> LENGTH: 377
<212> TYPE: PRT
<213> ORGANISM: Artificial Sequence
<220> FEATURE:
<223> OTHER INFORMATION: Synthetic Polypeptide

<400> SEQUENCE: 3

Gly Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
                20                  25                  30

Ser Glu Leu Thr Gln Gln Leu Asn Ala Leu Phe Gln Asp Lys Leu Gly
            35                  40                  45

Glu Val Asn Thr Tyr Ala Gly Asp Leu Gln Lys Lys Leu Val Pro Phe
        50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Glu Leu Arg Ala Arg Leu Leu Pro
                85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
    130                 135                 140

Met Glu Arg Val Leu Arg Glu Asn Ala Asp Ser Leu Gln Ala Ser Leu
145                 150                 155                 160

Arg Pro His Ala Asp Glu Leu Lys Ala Lys Ile Asp Gln Asn Val Glu
                165                 170                 175

Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
```

```
                       245                 250                 255
Gly Asn Leu Arg Gly Asn Thr Glu Gly Leu Gln Lys Ser Leu Ala Glu
                260                 265                 270

Leu Gly Gly His Leu Asp Gln Gln Val Glu Glu Phe Arg Arg Arg Val
            275                 280                 285

Glu Pro Tyr Gly Glu Asn Phe Asn Lys Ala Leu Val Gln Gln Met Glu
        290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Thr Leu Ser Leu Pro
            340                 345                 350

Glu Leu Glu Gln Gln Gln Glu Gln Gln Gln Glu Gln Gln Gln Glu Gln
        355                 360                 365

Val Gln Met Leu Ala Pro Leu Glu Ser
370                 375
```

<210> SEQ ID NO 4
<211> LENGTH: 377
<212> TYPE: PRT
<213> ORGANISM: Homo sapiens
<220> FEATURE:
<221> NAME/KEY: VARIANT
<222> LOCATION: (1)..(1)
<223> OTHER INFORMATION: X is G, A, V or absent
<220> FEATURE:
<221> NAME/KEY: VARIANT
<222> LOCATION: (166)..(166)
<223> OTHER INFORMATION: X is E or K
<220> FEATURE:
<221> NAME/KEY: VARIANT
<222> LOCATION: (348)..(348)
<223> OTHER INFORMATION: X is T or S
<220> FEATURE:
<221> NAME/KEY: VARIANT
<222> LOCATION: (361)..(361)
<223> OTHER INFORMATION: X is Q or H

<400> SEQUENCE: 4

```
Xaa Glu Val Ser Ala Asp Gln Val Ala Thr Val Met Trp Asp Tyr Phe
1               5                   10                  15

Ser Gln Leu Ser Asn Asn Ala Lys Glu Ala Val Glu His Leu Gln Lys
                20                  25                  30

Ser Glu Leu Thr Gln Gln Leu Asn Ala Leu Phe Gln Asp Lys Leu Gly
            35                  40                  45

Glu Val Asn Thr Tyr Ala Gly Asp Leu Gln Lys Lys Leu Val Pro Phe
        50                  55                  60

Ala Thr Glu Leu His Glu Arg Leu Ala Lys Asp Ser Glu Lys Leu Lys
65                  70                  75                  80

Glu Glu Ile Gly Lys Glu Leu Glu Glu Leu Arg Ala Arg Leu Leu Pro
                85                  90                  95

His Ala Asn Glu Val Ser Gln Lys Ile Gly Asp Asn Leu Arg Glu Leu
            100                 105                 110

Gln Gln Arg Leu Glu Pro Tyr Ala Asp Gln Leu Arg Thr Gln Val Asn
        115                 120                 125

Thr Gln Ala Glu Gln Leu Arg Arg Gln Leu Thr Pro Tyr Ala Gln Arg
130                 135                 140

Met Glu Arg Val Leu Arg Glu Asn Ala Asp Ser Leu Gln Ala Ser Leu
145                 150                 155                 160
```

Arg Pro His Ala Asp Xaa Leu Lys Ala Lys Ile Asp Gln Asn Val Glu
                165                 170                 175

Glu Leu Lys Gly Arg Leu Thr Pro Tyr Ala Asp Glu Phe Lys Val Lys
            180                 185                 190

Ile Asp Gln Thr Val Glu Glu Leu Arg Arg Ser Leu Ala Pro Tyr Ala
        195                 200                 205

Gln Asp Thr Gln Glu Lys Leu Asn His Gln Leu Glu Gly Leu Thr Phe
    210                 215                 220

Gln Met Lys Lys Asn Ala Glu Glu Leu Lys Ala Arg Ile Ser Ala Ser
225                 230                 235                 240

Ala Glu Glu Leu Arg Gln Arg Leu Ala Pro Leu Ala Glu Asp Val Arg
                245                 250                 255

Gly Asn Leu Arg Gly Asn Thr Glu Gly Leu Gln Lys Ser Leu Ala Glu
            260                 265                 270

Leu Gly Gly His Leu Asp Gln Gln Val Glu Glu Phe Arg Arg Arg Val
        275                 280                 285

Glu Pro Tyr Gly Glu Asn Phe Asn Lys Ala Leu Val Gln Gln Met Glu
    290                 295                 300

Gln Leu Arg Gln Lys Leu Gly Pro His Ala Gly Asp Val Glu Gly His
305                 310                 315                 320

Leu Ser Phe Leu Glu Lys Asp Leu Arg Asp Lys Val Asn Ser Phe Phe
                325                 330                 335

Ser Thr Phe Lys Glu Lys Glu Ser Gln Asp Lys Xaa Leu Ser Leu Pro
            340                 345                 350

Glu Leu Glu Gln Gln Gln Gln Xaa Gln Glu Gln Gln Gln Glu Gln
        355                 360                 365

Val Gln Met Leu Ala Pro Leu Glu Ser
    370                 375

<210> SEQ ID NO 5
<211> LENGTH: 1125
<212> TYPE: DNA
<213> ORGANISM: Homo sapiens

<400> SEQUENCE: 5
gtcagtgctg accaggtggc cacagtgatg tgggactact tcagccagct gagcaacaat      60
gccaaggagg ccgtggaaca tctccagaaa tctgaactca cccagcaact caatgccctc     120
ttccaggaca aacttggaga agtgaacact tacgcaggtg acctgcagaa gaagctggtg     180 cccctttgcca ccgagctgca tgaacgcctg gccaaggact cggagaaact gaaggaggag     240
attgggaagg agctggagga gctgagggcc cggctgctgc ccatgccaa tgaggtgagc     300 cagaagatcg gggacaacct gcgagagctt cagcagcgcc tggagcccta cgcggaccag     360
ctgcgcaccc aggtcaacac gcaggccgag cagctgcggc cccagctgac cccctacgca     420
cagcgcatgg agagagtgct gcgggagaac gccgacagcc tgcaggcctc gctgaggccc     480
cacgccgacg agctcaaggc caagatcgac cagaacgtgg aggagctcaa gggacgcctt     540
acgccctacg ctgacgaatt caaagtcaag attgaccaga ccgtggagga gctgcgccgc     600
agcctggctc cctatgctca ggacacgcag gagaagctca ccaccagct gagggcctg     660 accttccaga tgaagaagaa cgccgaggag ctcaaggcca ggatctcggc cagtgccgag     720
gagctgcggc agaggctggc gcccttggcc gaggacgtgc gtggcaacct gaggggcaac     780
accgaggggc tgcagaagtc actggcagag ctggtgggc acctgaccca gcaggtggag     840

-continued

```
gagttccgac gccgggtgga gccctacggg gaaaacttca acaaagccct ggtgcagcag      900
atggaacagc tcaggcagaa actgggcccc catgcggggg acgtggaagg ccacctgagc      960
ttcctggaga aggacctgag ggacaaggtc aactccttct tcagcacctt caaggagaaa     1020
gagagccagg acaagactct ctccctccct gagctcgagc aacagcagga acagcagcag     1080
gagcagcagc aggagcaggt gcagatgctg gcccctttgg agagc                     1125
```

APOLIPOPROTEIN AIV AS AN ANTIDIABETIC PEPTIDE

RELATED APPLICATIONS

This application is a 35 U.S.C. §371 national stage filing of International Application No. PCT/US2012/021802, filed Jan. 19, 2012, which claims the benefit of U.S. Provisional Application No. 61/434,196, filed on Jan. 19, 2011, the entire teachings of which are incorporated herein by reference.

TECHNICAL FIELD

The present disclosure relates to a method of treating diabetes. More particularly, the present disclosure relates to a method of treating type two diabetes mellitus by administering an effective amount of apolipoprotein A-IV.

BACKGROUND

The occurrence of diabetes is widespread, with approximately 8% of the population in the United States suffering from diabetes. Diabetes is a chronic disease characterized by high blood sugar due to the body's inability to effectively produce and/or use insulin. Diabetes can lead to a variety of physical complications, including but not limited to renal failure, blindness, nerve damage, heart disease, sleep apnea, and celiac disease. For example, in the United States, diabetes is the leading cause of renal failure, blindness, amputation, stroke, and heart attack. Also in the United States, diabetes is the sixth leading cause of death and has been shown to reduce the life expectancy of middle-aged adults by about five to ten years.

The most common form of diabetes is type two diabetes mellitus (hereinafter "T2DM"). T2DM is characterized by hyperglycemia, insulin resistance, β-cell dysfunction, and dysregulated hepatic gluconeogenesis. Persons suffering from T2DM experience a loss of glucose-stimulated insulin secretion related to the impaired release of stored insulin granules from β-cells in the first phase of insulin secretion. In the second phase of insulin secretion, persons suffering from T2DM experience a gradual loss of the ability to actively synthesize insulin in response to glucose stimuli.

The prevalence of T2DM is increasing and in 2002, T2DM resulted in greater than $130 billion in health care expenses. As such, new therapies for effectively treating T2DM are needed.

SUMMARY

The present disclosure is based on the surprising discovery that apolipoprotein A-IV is an effective anti-diabetic peptide which is intimately involved in the resolution of T2DM. Apolipoprotein A-IV is a key gut hormone which contributes to post-prandial glucose tolerance and acts as a previously unappreciated mediator in the improvement of glucose tolerance. Accordingly, in one embodiment, methods of treating T2DM in a subject in need thereof are disclosed. The method comprises administering to the subject an effective amount of an apolipoprotein A-IV or a biologically active analogue thereof having at least 90, 95, 96, 97, 98 or 99% identity to the apolipoprotein A-IV.

In another embodiment, a pharmaceutical composition comprising apolipoprotein A-IV is disclosed. The pharmaceutical composition comprises an apolipoprotein A-IV or a biologically active analogue thereof having at least 90, 95, 96, 97, 98 or 99% identity to the apolipoprotein A-IV formulated for administration to a subject for the treatment of T2DM.

In yet another embodiment, a method for substantially restoring glucose tolerance in a subject in need thereof to a normal level is disclosed. The method comprises administering to the subject an effective amount of an apolipoprotein A-IV or a biologically active analogue thereof having at least 90, 95, 96, 97, 98 or 99% identity to an apolipoprotein A-IV, for example, by systemic administration of the apolipoprotein A-IV or the biologically active analogue thereof.

In yet still another embodiment, a method for lowering blood glucose level in a subject in need thereof is disclosed. The method comprises administering to the subject an effective amount of apolipoprotein A-IV or a biologically active analogue thereof having at least 90, 95, 96, 97, 98 or 99% identity to the apolipoprotein A-IV to the subject in need, for example, by systemic administration. An "effective amount" is as described below and includes about 0.25 to 2 µg/g of the apoA-IV or the biologically active analogue thereof.

These and other features and advantages of these and other various embodiments according to the present disclosure will become more apparent in view of the drawings, detailed description, and claims provided herein.

BRIEF DESCRIPTION OF THE DRAWINGS

The following detailed description of the embodiments of the present disclosure can be better understood when read in conjunction with the following drawings, where like structure is indicated with like reference numerals, and in which:

FIG. 15 is a protein with the amino acid sequence of full length wild type human apolipoprotein A-IV (SEQ ID NO. 1).

FIG. 16 is a protein with the amino acid sequence of full length wild type mouse apolipoprotein A-IV (SEQ ID NO. 2).

FIG. 17 is a protein with the amino acid sequence of full length wild type human apolipoprotein A-IV with the addition of glycine at the N-terminus (SEQ ID NO. 3).

FIG. 18 is a protein with the amino acid sequence of human apolipoprotein A-IV showing polymorphic substitutions T347S, Q360H, and/or E165K and the optional addition of glycine, alanine or valine to the N-terminus (SEQ ID NO. 4).

FIG. 19 is a polynucleotide (SEQ ID NO. 5) encoding full length wild type human apolipoproteom A-IV.

Figure 1:
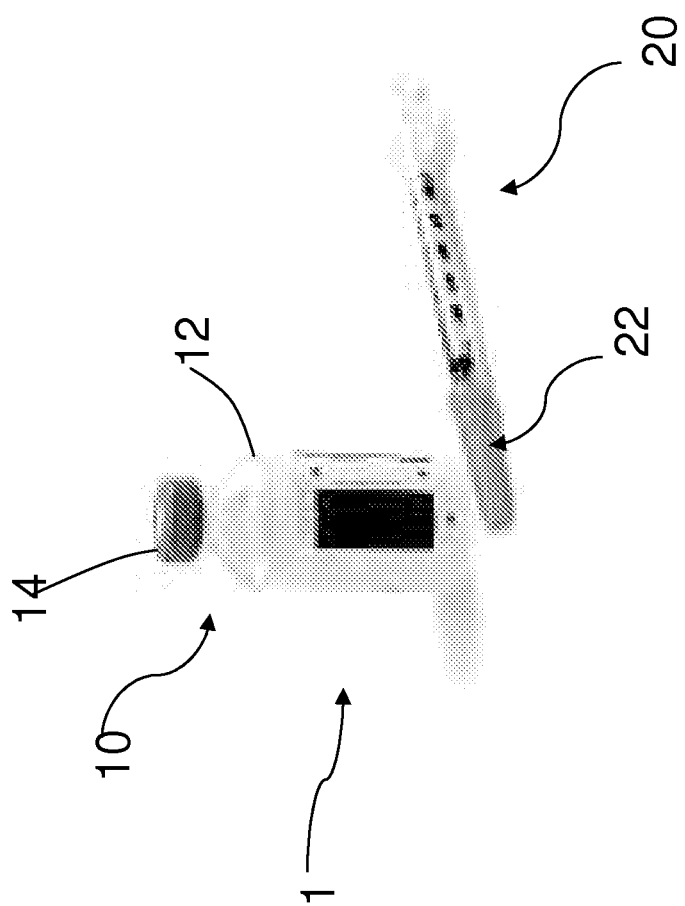
FIG. 1 is a side perspective view of a device having a reservoir of a pharmaceutical composition and a syringe according to an embodiment of the present disclosure.

Skilled artisans appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments of the present disclosure.

DETAILED DESCRIPTION

The following terms are used in the present application:

As used herein, the term "effective amount" describes the amount necessary or sufficient to realize a desired biologic effect. The effective amount for any particular application may vary depending on a variety of factors, including but not limited to the particular composition being administered, the size of the subject, and/or the severity of the disease and/or condition being treated. In one embodiment, an "effective amount" is a dose of about 0.25 to 10 μg/g of an apolipoprotein A-IV or biologically active analogue thereof. Alternatively, an "effective amount of an apoA-IV or a biologically active analogue thereof is about 1 to 10 μg/g, about 0.25 to 2 μg/g, or about 1 μg/g. An apoA-IV or a biologically active analogue is administered one time daily. Alternatively, an apoA-IV or a biologically active analogue thereof is administered about 2 times per day. In yet another alternative, an apoA-IV or a biologically active analogue thereof is administered more than twice a day, for example, three times per day. In yet another alternative, apoA-IV is administered once every second, third, fourth, fifth or sixth day, or once weekly.

As used herein, the term "desired biologic effect" describes reducing the effects of, counteracting, and/or eliminating a disease or condition. For example, in the context of T2DM, desired biologic effects include, but are not limited to lowering blood glucose, improving glucose tolerance, substantially restoring glucose tolerance to a normal level, improving insulin secretion, and/or substantially restoring insulin secretion to a normal level.

As used herein, the term "normal level" describes a level that is substantially the same as the level in a subject who is not in need of treatment. For example, in the context of treating T2DM, a normal level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In another example in the context of treating T2DM, a normal level of glucose tolerance describes the ability of the subject to metabolize carbohydrates such that the level of blood glucose is from about 70 mg/dL to about 130 mg/dL before meals and less than about 180 mg/dL about one to two hours after meals, or from about 70 mg/dL to about 100 mg/dL before meals and less than about 140 mg/dL about one to two hours after meals. In still another example in the context of treating T2DM, the normal level of insulin secretion is the amount required to maintain a normal level of glucose tolerance, wherein the level of insulin secretion is greater than about 1 ng/mL about fifteen hours after meals.

In the context of blood glucose level, the term "restore" describes changing the blood glucose level of a subject to a normal level. Similarly, in the context of glucose tolerance, the term "restore" describes changing the glucose tolerance of a subject to a normal level. Also, in the context of insulin secretion, "restore" describes changing the insulin secretion of a subject to a normal level.

In the context of apolipoprotein A-IV, the term "biologically active fragment" describes a fragment of apolipoprotein A-IV which is capable of realizing a desired biologic effect in a subject with T2DM. The term "biologically active analogue" describes an analogue of an apolipoprotein A-IV which is capable of realizing a desired biologic effect in a subject with T2DM. In one example, a desired biological effect is to restore glucose tolerance in apoA-IV knockout mice as described in Example 2. Another example of a desired biological effect is to cause a statistically significant lowering of abnormal glucose levels in an animal model of T2DM, such as the mouse model described in Example 7.

As used herein, the term "obese" describes a condition in which a subject is well above a normal weight. In one specific example, the term obese describes a condition in which a subject is more than about 20% over their ideal weight and/or has a body mass index of about thirty or greater than about thirty. In one embodiment, the subject being treated is obese; in another embodiment, the subject being treated is not obese; and in yet another embodiment, the subject being treated has a normal body weight.

Embodiments of the present disclosure relate to methods for treating T2DM in a subject in need thereof and pharmaceutical compositions for the treatment of T2DM. In one embodiment, a method of treating diabetes is disclosed. In one particular embodiment, a method of treating T2DM in a subject in need thereof is disclosed, wherein the method comprises administering an effective amount of an apolipoprotein A-IV (hereinafter "apoA-IV") or a biologically active analogue thereof to the subject.

In one embodiment, the method of treating T2DM is effective to lower blood glucose level of a subject. In one particular embodiment, the method is effective to lower blood glucose level of a subject by about 20 to 50%. In a further embodiment, the method is effective to lower the blood glucose level of a subject by about 40%. In still a further embodiment, the method is effective to substantially restore blood glucose level to a normal level.

In another embodiment, the method of treating T2DM is effective to substantially restore glucose tolerance of a subject to a normal level. In one particular embodiment, the method is effective to substantially restore glucose tolerance of a subject to a normal level within about two hours after administration of a dose of an apoA-IV or a biologically active analogue thereof. In another embodiment, the glucose tolerance of a subject is substantially restored to a normal level for about eight to twelve hours.

In yet another embodiment, the treatment is effective to substantially restore insulin secretion to a normal level. In one particular embodiment, the treatment is effective to substantially restore insulin secretion to a normal level within about two hours after the administration of a dose of an apoA-IV or a biologically active analogue thereof. In another embodiment, insulin secretion is substantially restored to a normal level for about eight to twelve hours. In still another embodiment, the treatment is effective to lower the level of C-reactive protein.

In one embodiment, an apoA-IV or a biologically active analogue thereof is administered systemically. Systemic administration of the apoA-IV or the analogue thereof is selected from the group consisting of oral, subcutaneous, intravenous, intramuscular, and intraperitoneal administration.

In another embodiment, a pharmaceutical composition is disclosed. In one particular embodiment, the pharmaceutical composition comprises an apoA-IV or a biologically active analogue thereof. In another embodiment, the apoA-IV or analogue thereof is formulated for administration to a subject for the treatment of T2DM. In this particular embodiment, a method for treating T2DM in a subject in need thereof is also provided, wherein the method comprises administering an effective amount of the pharmaceutical composition to the subject.

An "apolipoprotein A-IV" (also referred to herein as "apoA-IV") refers to mammalian apoA-IV and includes full-length apoA-IV and biologically active fragments of apoA-IV. The full-length human apoA-IV is a 376 amino acid protein (SEQ ID NO: 1), the amino acid sequence of which is shown in FIG. 15; the amino acid sequence of full length mouse apoA-IV (SEQ ID NO. 2) is shown in FIG. 16. Also encompassed by the term "apolipoprotein A-IV" is the known analogue in which a glycine is added to N-terminus of the apolipoprotein A-IV of the full length human sequence (SEQ ID NO. 3, as shown in FIG. 17), and analogues thereof having conservative substitutions for the N-terminal glycine (such as alanine and valine). An "apolipoprotein A-IV" also includes polymorphic forms thereof, including the T347S, Q360H, or E165K substitutions to the human sequence represented by SEQ ID NO. 1 or the corresponding positions of SEQ ID NO. 3. As such, "apolipoprotein A-IV" includes the protein of SEQ ID NO. 4, shown in FIG. 18.

A biologically active analogue of apolipoprotein A-IV has at least 90, 95, 96, 97, 98 or 99% identity to an apolipoprotein A-IV. As described in the previous paragraph, an apolipoprotein A-IV includes full length mammalian apolipoprotein A-IV (e.g., human or mammalian), polymorphic forms thereof, the protein of SEQ ID NOS. 3 and 4 and biologically active fragments of any of the foregoing Amino acid variations in the biologically active analogues preferably have conservative substitutions relative to the wild type sequences.

A "conservative substitution" is the replacement of an amino acid with another amino acid that has the same net electronic charge and approximately the same size and shape Amino acid residues with aliphatic or substituted aliphatic amino acid side chains have approximately the same size when the total number of carbon and heteroatoms in their side chains differs by no more than about four. They have approximately the same shape when the number of branches in their side chains differs by no more than one Amino acid residues with phenyl or substituted phenyl groups in their side chains are considered to have about the same size and shape. Listed below are five groups of amino acids. Replacing an amino acid residue with another amino acid residue from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

An apolipoprotein A-IV or a biologically active analogue thereof can be glycosylated or unglycosylated. The preparation of recombinant unglycosylated human and mouse apolipoprotein A-IV is described in Example 11. The polynucleotide sequence of full length wild type human apolipoprotein (SEQ ID NO. 1) is shown as SEQ ID NO. 4 in FIG. 18. Apolipoprotein A-IV used in examples 1-10 is unglycosylated. The apoA-IV may be prepared according to a method known in the molecular biology field. For example, apoA-IV may be prepared via traditional molecular cloning techniques.

Apolipoprotein A-IV knockout mice used in the examples were generated according to procedures disclosed in *J Lipid Res.* 1997 September; 38(9):1782-94, the entire teachings of which are incorporated herein by reference.

In one particular embodiment, the pharmaceutical composition may further comprise a pharmaceutically acceptable carrier. Pharmaceutically acceptable carriers include a wide range of known diluents (i.e., solvents), fillers, extending agents, binders, suspending agents, disintegrates, surfactants, lubricants, excipients, wetting agents and the like commonly used in this field. The pharmaceutical composition is preferably aqueous, i.e., is a liquid formulation, and preferably comprises pyrogen free water. These carriers may be used singly or in combination according to the form of the pharmaceutical preparation. The resulting preparation may incorporate, if necessary, one or more solubilizing agent, buffers, preservatives, colorants, perfumes, flavorings and the like that are widely used in the field of pharmaceutical preparation.

The apolipoprotein A-IV or biologically active analogue thereof may be formulated into a dosage form selected from the group consisting of tablets, capsules, granules, pills, injections, solutions, emulsions, suspensions, and syrups.

The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The pharmaceutical composition of the invention for treating T2DM may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The proportion of the active ingredient to be contained in the pharmaceutical composition of the invention for treating diabetes can be suitably selected from a wide range.

In one particular embodiment, the subject in need of treatment of T2DM is a mammal. The mammal may be selected from the group consisting of humans, non-human primates, canines, felines, murines, bovines, equines, porcines, and lagomorphs. In one specific embodiment, the mammal is human. In another embodiment, apoA-IV or a biologically active analogue thereof may be administered to a subject for the treatment of T2DM wherein the subject is obese. Alternatively, apoA-IV may be administered to a subject for the treatment of T2DM wherein the subject is not obese.

Referring to FIG. 1, in yet another embodiment, a device 1 is disclosed. In one embodiment, the device 1 comprises a reservoir 10 of the pharmaceutical composition previously discussed above. In a further embodiment, the reservoir 10 comprises a vial 12. The vial 12 may be formed of any material that does not inhibit the function of the pharmaceutical composition. For example, the vial 12 may comprise glass and/or plastic. Additionally, the vial 12 may comprise a pierceable septum 14 through which the pharmaceutical composition may be removed. In use, the septum 14 of the vial is pierced by the needle 22 of a syringe 20, the pharmaceutical composition is removed by the syringe 20 from the vial 12, and the pharmaceutical composition is administered via injection to a subject in need.

EXAMPLES

The following non-limiting examples illustrate the methods of the present disclosure.

Example 1

Glucose Intolerance of ApoA-IV Knockout Mice

Experimental Protocol. Male apoA-IV knockout ("hereinafter "KO") mice were obtained. Wild-type (hereinafter "WT") mice served as controls. ApoA-IV KO and WT mice were obtained from a colony kept at the University of Cincinnati (Cincinnati, Ohio). ApoA-IV KO and WT mice were fed a chow diet. Prior to performing the glucose tolerance tests, ApoA-IV KO mice and WT mice were fasted for five hours. In the glucose tolerance tests, the apoA-IV KO mice and WT mice were injected intraperitoneally with a dose of about 2 mg/g body weight of glucose and plasma glucose was measured at about 0, 15, 30, 60, and 120 minutes following the injection of glucose. The glucose tolerance tests were performed twice, once at three months of age and again at sixteen months of age.

Figure 2:
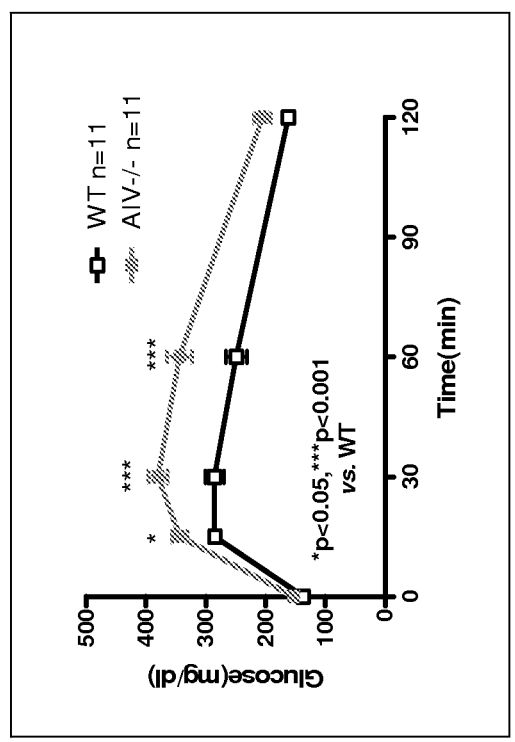
FIG. 2 is a graph of plasma glucose (mg/dL) in male apolipoprotein A-IV knockout and wild-type mice with respect to time (mg/dL) for an intraperitoneal glucose tolerance test.
Figure 3:
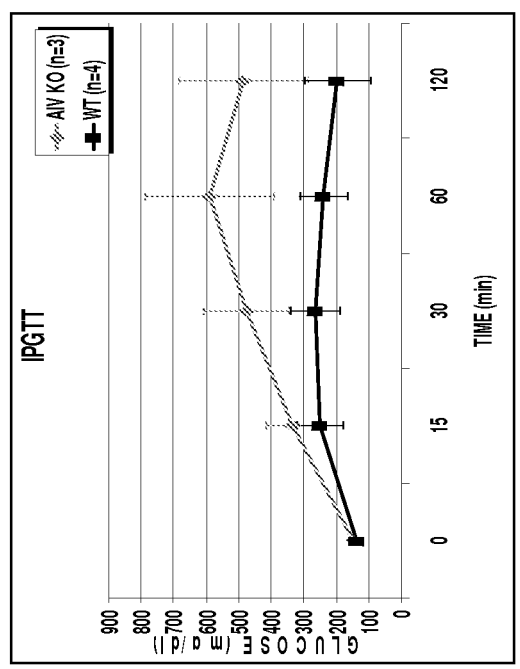
FIG. 3 is a graph of plasma glucose (mg/dL) with respect to time (min) for an intraperitoneal glucose tolerance test in apolipoprotein A-IV wild-type and knockout animals at 16 months of age.

Experimental Results. As shown in FIG. 2, apoA-IV KO mice were glucose intolerant relative to the WT mice. Specifically, FIG. 2 shows that plasma glucose levels in WT mice were lower than plasma glucose levels in apoA-IV KO mice for two hours following intraperitoneal injection with glucose. While not being bound by the theory, the implication of these studies was that apoA-IV is necessary for normal glucose homeostasis (at least in males). Moreover, as shown in FIG. 3, apoA-IV KO mice demonstrated an increased glucose intolerance when tested at sixteen months of age. Specifically, FIG. 3 shows that plasma glucose levels in apoA-IV KO mice tested at sixteen months of age were higher than the plasma glucose levels in apoA-IV KO tested at three months of age. While not being bound by the theory, the implication of these studies was that glucose tolerance of apoA-IV KO mice worsens with age.

Experiment with Female Wild Type and ApoA-IV Knockout Mice

Figure 11:
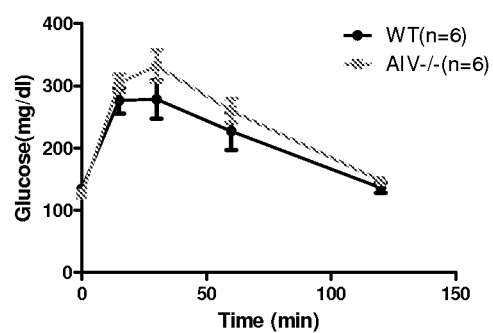
FIG. 11 is a graph of plasma glucose (mg/dL) in female apolipoprotein A-IV knockout and wild-type mice with respect to time (mg/dL) during an intraperitoneal glucose tolerance test (IPGTT).

Female ApoA-IV wildtype and knockout mice were subjected to the same inraperitoneal glucose itolerance test as was used for the male apoA-IV KO and WT mice, as described earlier in this Example 1. The results are shown in FIG. 11. Female apoA-IV$^{-/-}$ mice, when challenged intraperitoneally with glucose, have increased plasma glucose levels compared with female WT animals, but there is no statistical significant difference. On the other hand, the males have a significant difference between WT and KO animals.

Example 2

Restoration of Glucose Tolerance in ApoA-IV Knockout Mice

Experimental Protocol. Upon demonstrating that apoA-IV KO mice are glucose intolerant, a series of extensive studies were performed to determine whether administration of apoA-IV to apoA-IV KO mice would restore glucose tolerance to a normal level. Specifically, a series of studies were performed to determine not only the amount of apoA-IV to be administered but also the optimal time in which to administer apoA-IV prior to conducting glucose tolerance tests.

ApoA-IV male KO mice were injected intraperitoneally with doses of about 0.25, 0.5, 1, and 2 µg/g by weight of apoA-IV. ApoA-IV KO mice were also injected intraperitoneally with saline solution to serve as a control. Following injection with mouse apoA-IV or saline solution, glucose tolerance tests were conducted at three months of age as previously discussed. Specifically, glucose tolerance tests were conducted about two hours following injection with apoA-IV or saline solution. Experimental results indicated that the optimal time to restore glucose tolerance in apoA-IV KO mice was to administer apoA-IV about two hours prior to conducting glucose tolerance tests.

Figure 4:
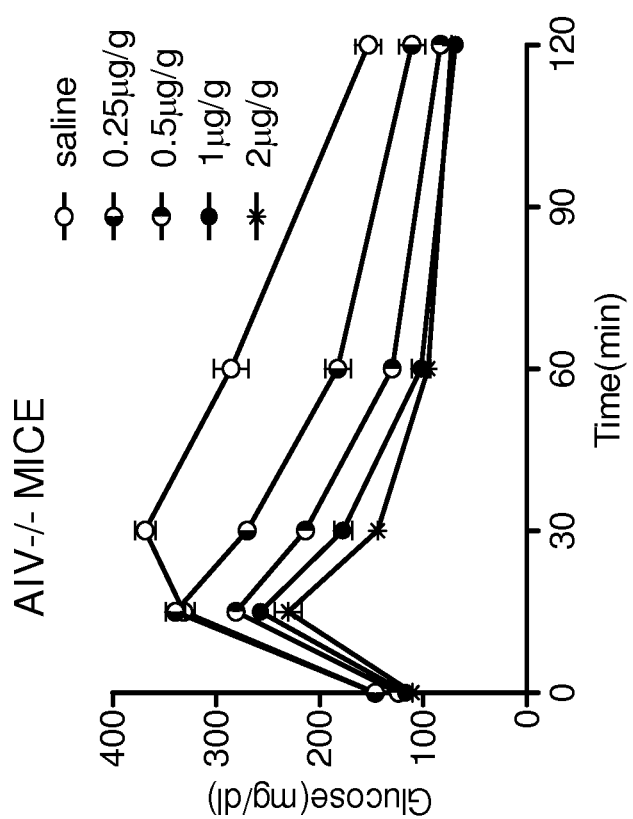
FIG. 4 is a graph of plasma glucose (mg/dL) with respect to time (min) in male apolipoprotein A-IV knockout mice following the intraperitoneal administration of recombinant apolipoprotein A-IV (µg/g) or saline solution for an intraperitoneal glucose tolerance test.

Experimental Results. As shown in FIG. 4, the administration of apoA-IV to apoA-IV KO mice restored glucose tolerance to a normal level. Specifically, FIG. 4 shows that plasma glucose levels in apoA-IV KO mice injected with apoA-IV were lower than plasma glucose levels in apoA-IV KO mice injected with saline solution. Moreover, as shown in FIG. 4, plasma glucose levels in apoA-IV KO mice injected with apoA-IV were the lowest in the apoA-IV KO mice injected with the highest dosage of apoA-IV; similarly, plasma glucose levels in apoA-IV KO mice injected with apoA-IV were the highest in the apoA-IV KO mice injected with the lowest dosage of apoA-IV. Accordingly, it was discovered that the degree of improvement of glucose tolerance was dependent on the dose of apoA-IV administered, with higher doses resulting in improved glucose tolerance.

Example 3

Specificity of ApoA-IV in Restoring Glucose Tolerance in ApoA-IV Knockout Mice Experimental Protocol. In order to assess the specificity of apoA-IV, we administered apolipoprotein AI (hereinafter "apoA-I") to apoA-IV KO mice. ApoA-I is a protein made by the small intestinal epithelial cells which also produce apoA-IV. ApoA-I shares many of the functions of apoA-IV. ApoA-IV KO mice were injected intraperitoneally with a dose of 1 μg/g by weight of apoA-I. ApoA-IV KO mice were also injected intraperitoneally with saline solution to serve as a control. Following injection with apoA-I or saline solution, glucose tolerance tests were conducted at three months of age as previously discussed. Specifically, glucose tolerance tests were conducted about two hours following injection with apoA-I or saline solution.

Figure 5:
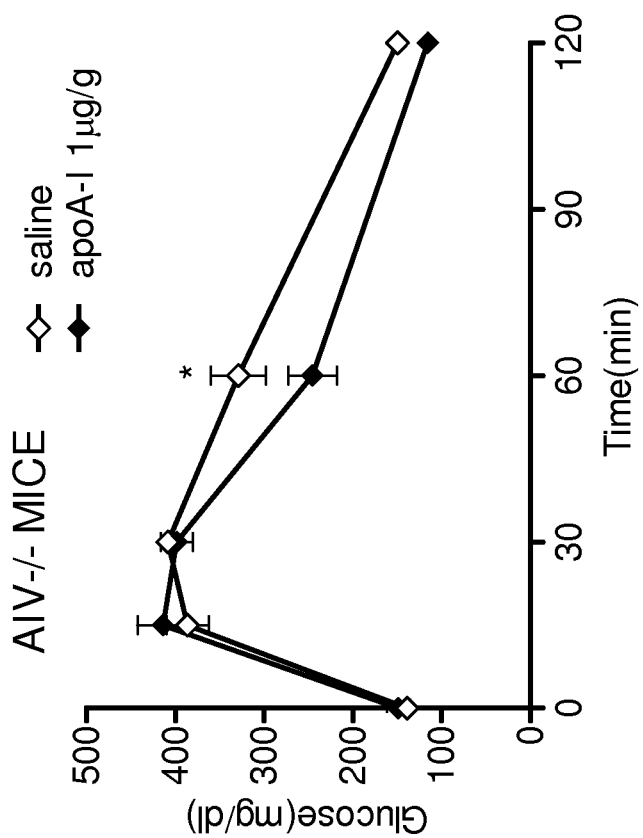
FIG. 5 is a graph of plasma glucose (mg/dL) with respect to time (min) in apolipoprotein A-IV knockout mice following the intraperitoneal administration of recombinant apolipoprotein A-I or saline solution for an intraperitoneal glucose tolerance test.

Experimental Results. As shown in FIG. 5, the administration of apoA-I to apoA-IV KO mice failed to restore or improve glucose tolerance.

Example 4

Mechanism of Restoration of Glucose Tolerance in ApoA-IV Knockout Mice

Experimental Protocol. In order to assess the mechanism by which ApoA-IV improves glucose tolerance in apoA-IV KO mice, we measured glucose-induced insulin secretion in apoA-IV KO mice. More specifically, we measured glucose-induced insulin secretion during glucose tolerance tests at three months of age as previously discussed. In this study, apoA-IV KO mice were injected intraperitoneally with a dose of about 1 μg/g by weight of mouse apoA-IV two hours prior to conducting the glucose tolerance tests. ApoA-IV KO mice were injected with saline solution about two hours prior to conducting glucose tolerance tests to serve as a control.

Figure 6:
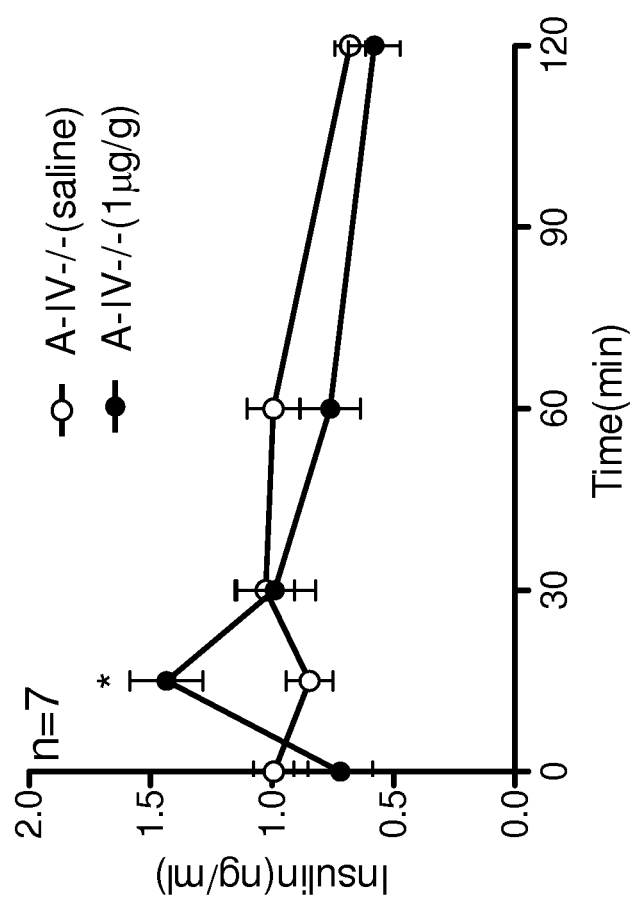
FIG. 6 is a graph of insulin secretion (ng/mL) with respect to time (min) in apolipoprotein A-IV knockout mice following the intraperitoneal administration of recombinant apolipoprotein A-I or saline solution.

Experimental Results. As shown in FIG. 6, phase I insulin secretion was absent in apoA-IV KO mice injected with saline solution. However, as shown in FIG. 6, phase I insulin secretion was restored in apoA-IV KO mice when apoA-IV was injected intraperitoneally two hours prior to performing the glucose tolerance tests.

Example 5

Efficacy of ApoA-IV in ApoA-IV Knockout and Wild-Type Mice on High Fat Diets Experimental Protocol. ApoA-IV KO and WT mice were chronically fed a high-fat semi-purified, nutritionally complete experimental diets (AIN-93M) purchased from Dyets (Bethlehem, Pa.) for 10 weeks. The high-fat diets contain about 20 g of fat (i.e. about 19 g of butter fat and 1 g of soybean oil to provide essential fatty acids) per 100 g of diet. The apoA-IV KO and WT mice were housed in individual tub cages with corncob bedding in a temperature- (about 22±1° C.) and light- (about 12 h light/12 dark) controlled vivarium. Glucose tolerance tests were performed at three months of age as previously discussed. Prior to performing the glucose tolerance tests, apoA-IV KO mice and WT mice were fasted for five hours. In the glucose tolerance tests, the apoA-IV KO mice and WT mice were injected intraperitoneally with a dose of about 2 mg/g body weight of glucose.

Figure 7:
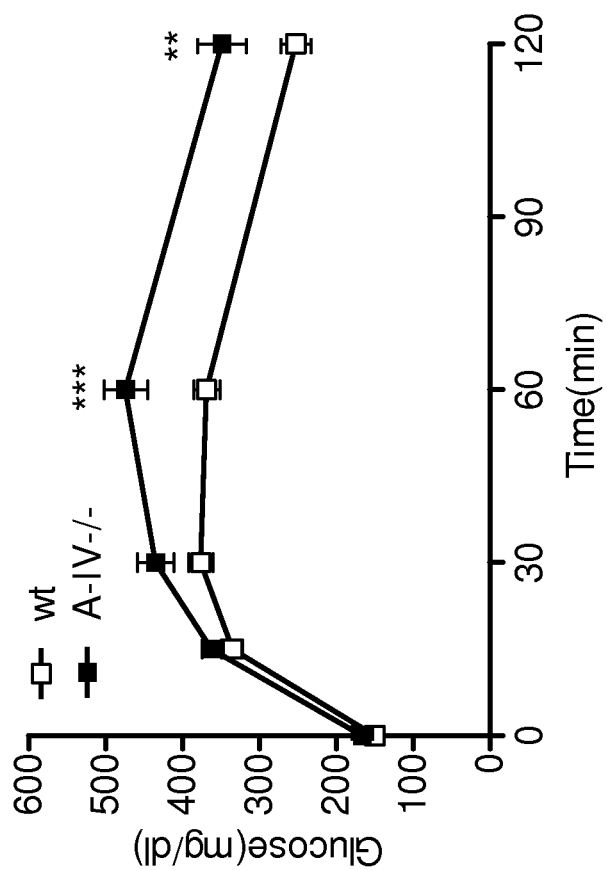
FIG. 7 is graph of plasma glucose (mg/mL) with respect to time (min) in apolipoprotein A-IV knockout and wild-type mice on a chronically high-fat diet for an intraperitoneal glucose tolerance test.

Experimental Results. As shown in FIG. 7, apoA-IV KO mice displayed greater glucose intolerance relative to the WT mice. Specifically, FIG. 7 shows that plasma glucose levels in WT mice were lower than plasma glucose levels in apoA-IV KO mice for two hours following intraperitoneal injection with glucose.

Example 6

Restoration of Glucose Tolerance in ApoA-IV Knockout and Wild-Type Mice on High Fat Diets Experimental Protocol. A series of studies were performed related to the administration of apoA-IV to apoA-IV KO and WT mice on high-fat diets for 14 weeks at three months of age (20% by weight of fat, 19% of butter fat and 1% of safflower oil). Specifically, apoA-IV KO and WT mice were injected intraperitoneally with a dose of about 1 μg/g body weight of mouse apoA-IV. ApoA-IV KO and WT mice were also injected intraperitoneally with saline solution to serve as a control. Following injection with apoA-IV or saline solution, glucose tolerance tests were conducted. Specifically, glucose tolerance tests were conducted two hours following injection with apoA-IV or saline solution.

Figure 8:
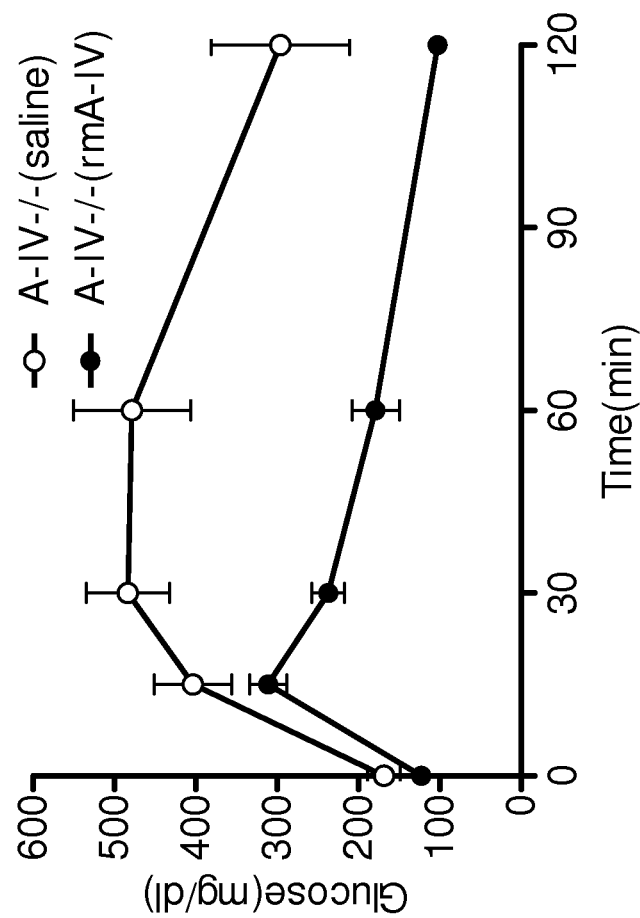
FIG. 8 is a graph of plasma glucose (mg/mL) with respect to time (min) in apolipoprotein A-IV knockout mice on a chronically high-fat diet following the intraperitoneal administration of recombinant mouse apolipoprotein A-IV (1 µg/g) or saline solution for an intraperitoneal glucose tolerance test.

Experimental Results. As shown in FIG. 8, the administration of apoA-IV in apoA-IV KO mice significantly improved glucose tolerance. Specifically, FIG. 8 shows that plasma glucose levels in apoA-IV KO mice injected with apoA-IV were lower than plasma glucose levels in apoA-IV KO mice injected with saline solution. [the previous sentence is redundant since the next sentence describes the same thing. Although the data is not included herein, it was also discovered that the administration of apoA-IV in WT mice fed chronically a high fat diet also significantly improved glucose tolerance.

Example 7

Restoration of Glucose Tolerance in Mice with T2DM

Experimental Protocol. In order to confirm that apoA-IV is effective in promoting glucose tolerance in animals with T2DM, heterozygous KK Cg-A/J (hereinafter "Cg-A/J") mice were obtained from Jackson Laboratories (Bar Harbor, Me.). Cg-A/J mice develop hyperglycemia, hyperinsulinemia, obesity, and glucose intolerance by eight weeks of age. The main cause of diabetes in these mice is insulin resistance produced by the polygenic interactions with the $A^y$ mutation, which encodes the agouti related protein and antagonist of the melanocortin-IV receptor. The Cg-A/J mice were fed chow diet. Additionally, there was a marked increase in blood glucose from ten to fourteen weeks of feeding the chow diet.

At fourteen weeks of age, the Cg-A/J mice were administered either mouse apoA-IV (about 1 µg/g body weight) or saline solution (to serve as a control) via intraperitoneal injection. Plasma glucose was then determined at about 0, 0.5, 1, 2, 3, 4, 5, 7, 11, and 24 hours.

Figure 9:
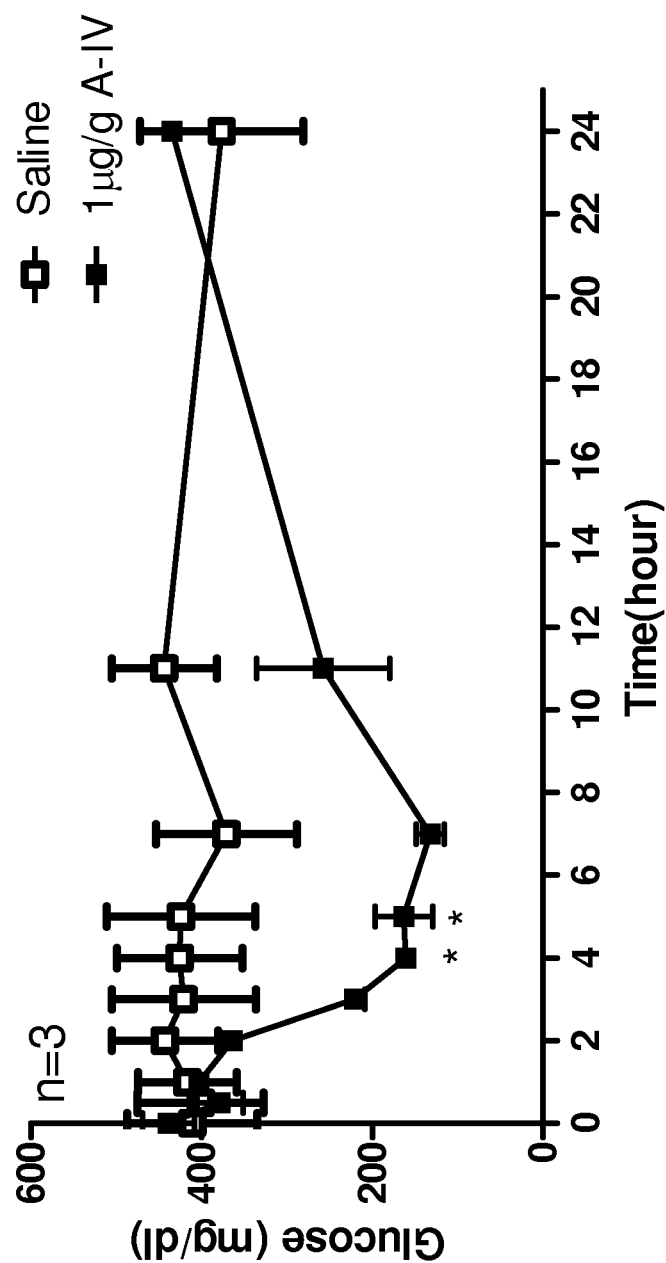
FIG. 9 is a graph of plasma glucose (mg/dL) with respect to time (h) in diabetic mice following the intraperitoneal administration of recombinant mouse apolipoprotein A-IV (1 μg/g) or saline solution for an intraperitoneal glucose tolerance test.

Experimental Results. As shown in FIG. 9, apoA-IV has a marked effect in lowering the blood sugar level of the Cg-A/J mice relative to the saline control. While the Cg-A/J mice injected with saline solution maintained a steady plasma glucose level throughout the 24 hour period of study, the Cg-A/J mice injected with apoA-IV experienced a decrease in plasma glucose for over 10 hours, and, during most of this period, the plasma glucose level was comparable to the C57BL/6J animals we have been studying. From this study, we conclude that the administration of apoA-IV is effective in lowering the plasma glucose in Cg-A/J mice.

Example 8

Level of Serum Amyloid P Component in ApoA-IV KO, ApoA-I KO, and WT Mice

Experimental Protocol. A series of studies were performed in related to determining the level of serum amyloid A protein component (hereinafter "SAP") in apoA-IV KO, apoA-I KO, and WT mice on atherogenic diets. The apoA-IV KO, apoA-I KO, and WT mice were obtained from the University of Cincinnati. SAP is a serum form of amyloid P component (hereinafter "AP"), a 25 kDa pentameric protein first identified as the pentagonal constituent of in vivo pathological deposits called amyloid. SAP behaves like C-reactive protein in humans. Specifically, the level of plasma SAP in apoA-IV KO, apoA-I KO, and WT mice was determined in apoA-IV KO, apoA-I KO, and WT mice after 12 weeks on an atherogenic diet. The level of plasma SAP was determined via Western blot analysis.

Figure 10:
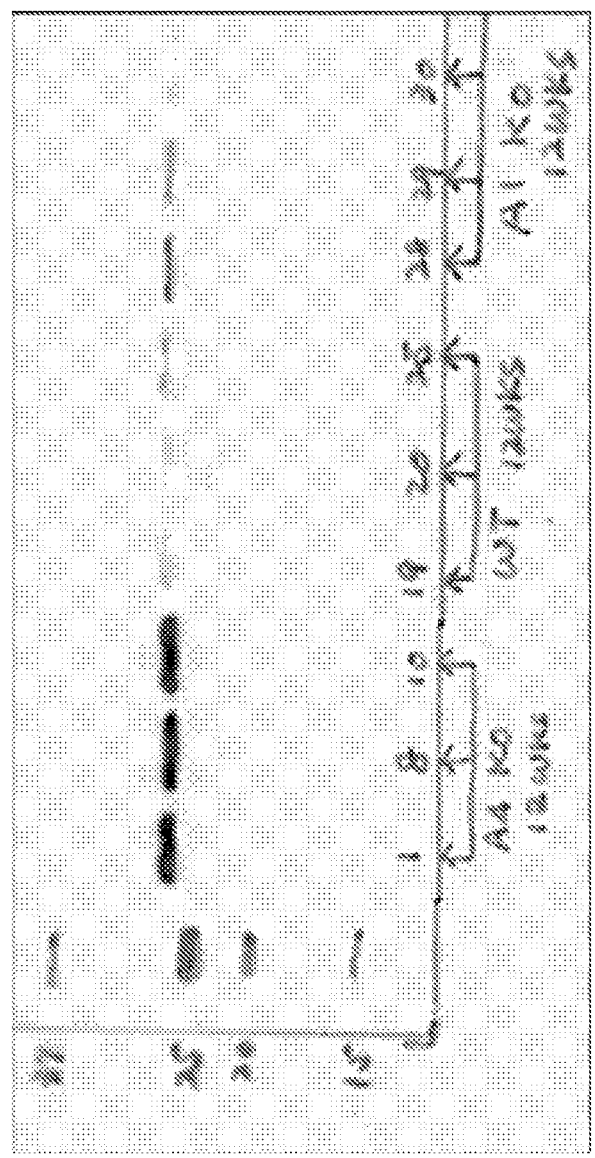
FIG. 10 depicts the results of a Western blot analysis of the level of serum amyloid A protein component in apolipoprotein A-IV knockout mice, wild-type mice, and apolipoprotein A-I knockout mice.

Experimental Results. As shown in FIG. 10, the level of SAP in apoA-IV KO mice (corresponding to mouse numbers 1, 8, and 10) increased relative to the level of SAP in apoA-I KO mice (corresponding to mouse numbers 28, 29, and 30) and WT mice (corresponding to mouse numbers 19, 20, and 25).

For the purposes of describing and defining the present disclosure it is noted that the terms "about" and "substantially" are utilized herein to represent the inherent degree of uncertainty that may be attributed to any quantitative comparison, value, measurement, or other representation. The terms "about" and "substantially" are also utilized herein to represent the degree by which a quantitative representation may vary from a stated reference without resulting in a change in the basic function of the subject matter at issue.

The above description and drawings are only to be considered illustrative of exemplary embodiments, which achieve the features and advantages of the present disclosure. Modification and substitutions the features and steps described can be made without departing from the intent and scope of the present disclosure. Accordingly, the disclosure is not to be considered as being limited by the foregoing description and drawings, but is only limited by the scope of the appended claims.

Example 8

Human ApoA-IV Lowers Blood Glucose Levels in Wild-Type Mice Undergoing Intraperitoneal Glucose Tolerance Testing Experimental Protocol. Studies were performed to determine whether administration of human apoA-IV to wild type mice would affect blood glucose levels in mice undergoing glucose tolerance testing.

Three month old wild type mice were injected intraperitoneally with doses of about 1 µg/g by weight of human apoA-IV. As a control, another group of wild type mice was injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Figure 12:
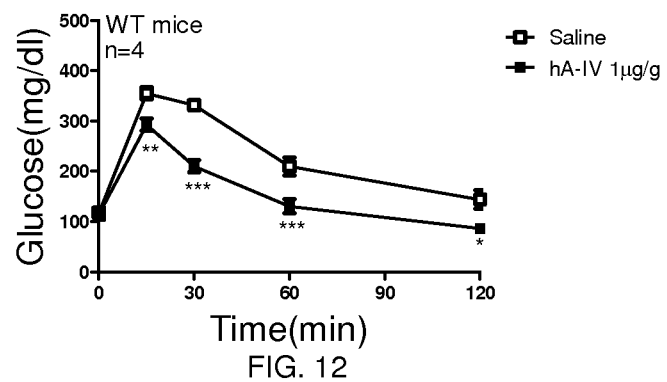
FIG. 12. is a graph of plasma glucose (mg/dL) with respect to time (mg/dL) in wild type mice following the intraperitoneal administration of 1.0 μg/g human apolipoprotein A-IV or saline solution during an intraperitoneal glucose tolerance test.

Experimental Results. As shown in FIG. 12, human apoA-IV was effective in lowering blood glucose in wild type mice undergoing glucose tolerance testing.

Example 9

Effect of Mouse ApoA-IV in Wild-Type Female Mice Undergoing Intraperitoneal Glucose Tolerance Testing Experimental Protocol. Studies were performed to determine whether administration of mouse apoA-IV to female wild type mice would affect blood glucose levels in mice undergoing glucose tolerance testing.

Three month old female wild type mice were injected intraperitoneally with doses of about 1 µg/g by weight of mouse apoA-IV. As a control, another group of female wild type mice were injected intraperitoneally with saline solution. Following injection with human apoA-IV or saline solution, glucose tolerance tests were conducted. Specifically, glucose tolerance tests were conducted about two hours following injection with apoA-IV or saline solution and after five hours of fasting. Tail blood was collected and measure by glucometer.

Figure 13:
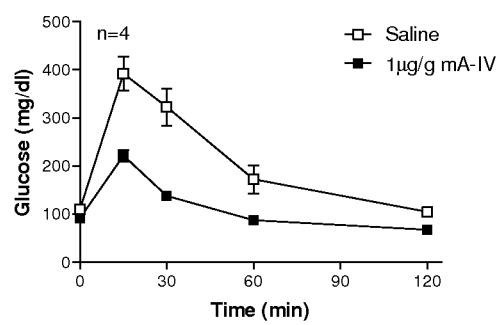
FIG. 13 is a graph of plasma glucose (mg/dL) with respect to time (min) in female wild type mice following the intraperitoneal administration of 1.0 μg/g recombinant mouse apolipoprotein A-IV or saline solution during an intraperitoneal glucose tolerance test.

Experimental Results. As shown in FIG. 13, mouse apoA-IV was effective in lowering blood glucose in wild type female mice undergoing glucose tolerance testing.

Example 10

Human ApoA-IV Stimulates Insulin Release in Human Islets

High purity human islets were provided by University of Virginia, Axon Cells. Islets were cultured in RPMI 1640, containing 10% FBS and 11 mM glucose at 37° C. in a humidified atmosphere of 95% air and 5% $CO_2$ for 48 hours. Four Groups of 50 IEQ islets were then pre-incubated at 37° C. for 1 h in regular KRB (129 mM NaCl, 4.8 mM KCl, 2.5 mM $CaCl_2$, 1.2 mM $MgSO_4$, 1.2 mM $KH_2PO_4$, 5 mM $NaHCO_3$, 10 mM HEPES and 0.2% BSA) containing 3.0 mM glucose. Islets in the first two groups were then incubated in regular KRB containing 3.0 mM glucose for an hour in the presence or absence of 10 µg/ml human A-IV and were further incubated with 20 mM glucose for an additional hour in the presence or absence of 10 μg/ml human A-IV. Islets in the last two groups were incubated in 30 mM KCl KRB (103.8 mM NaCl, 30 mM KCl, 2.5 mM $CaCl_2$, 1.2 mM $MgSO_4$, 1.2 mM $KH_2PO_4$, 5 mM $NaHCO_3$, 10 mM HEPES and 0.2% BSA) plus 250 μmol/l diazoxide containing 3.0 mM glucose for an hour in the presence or absence of 10 μg/ml human A-IV and were further incubated with 20 mM glucose for an additional hour in the presence or absence of 10 μg/ml human A-IV. Media were collected at the end of each one-hour incubation. Insulin levels were measured by ELISA kit (Millipore).

Figure 14:
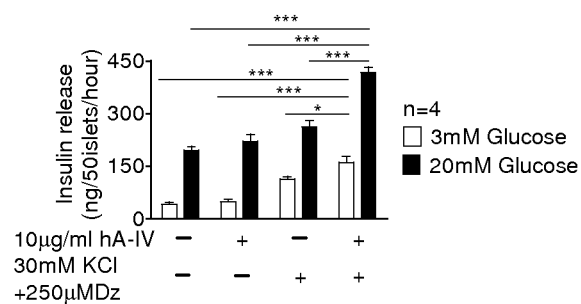
FIG. 14 is a bar graph showing the effect of 10 μg/g human apoA-IV on human islets depolarized by 30 mM KCl and 250 μM diazoxide in the presence of 3 mM or 20 mM glucose.

As can be seen from FIG. 14, when the human islets were maximally depolarized by 30 mM KCl plus 250 μM diazoxide, 10 μg/ml hA-IV showed a significant stimulatory effect on insulin secretion.

Example 11

Preparation of Unglycosylated ApoA-IV

Human and mouse apoA-IV cDNA was contained in a pSP65 maintenance vector, and an Afl III restriction site was engineered immediately 5' of the coding sequence for the mature apoA-IV protein. The gene was excised from the maintenance vector and ligated into the pET30 expression vector. The construct was transfected into *E. Coli* BL-21 (DE3) cells and grown in Luria-Bertani cultures supplemented with kanamycin (30 μg/ml) at 37° C. After induction of apoA-IV protein synthesis in the cells, the cells were harvested and sonicated. ApoA-IV protein from the lysate was purified by His-bind affinity column chromatography and dialysis. The resultant apoA-IV protein was diluted to a final concentration of 1.0 mg/ml in saline.

What is claimed is:

1. A method for treating type II diabetes mellitus in a subject in need thereof, the method comprising administering to the subject an effective amount of a polypeptide, wherein the amino acid sequence of the polypeptide is:

(SEQ ID NO. 3)
GEVSADQVATVMWDYFSQLSNNAKEAVEHLQKSELTQQLNALFQDKLGE

VNTYAGDLQKKLVPFATELHERLAKDSEKLKEEIGKELEELRARLLPHA

NEVSQKIGDNLRELQQRLEPYADQLRTQVNTQAEQLRRQLTPYAQRMER

VLRENADSLQASLRPHADELKAKIDQNVEELKGRLTPYADEFKVKIDQT

VEELRRSLAPYAQDTQEKLNHQLEGLTFQMKKNAEEELKARISASAEELR

QRLAPLAEDVRGNLRGNTEGLQKSLAELGGHLDQQVEEFRRRVEPYGEN

FNKALVQQMEQLRQKLGPHAGDVEGHLSFLEKDLRDKVNSFFSTFKEKE

SQDKTLSLPELEQQQEQQQEQQQEQVQMLAPLES.

2. The method of claim 1, wherein the subject is a human.
3. The method according to claim 2, wherein the polypeptide is glycosylated.
4. The method according to claim 2, wherein the polypeptide is unglycosylated.
5. The method according to claim 4, wherein the polypeptide is administered systemically.
6. The method according to claim 5, wherein the systemic administration of the polypeptide is selected from the group consisting of oral, subcutaneous, intravenous, intramuscular, and intraperitoneal administration.
7. The method according to claim 6, wherein the polypeptide is administered in a dose of about 1 to about 10 µg/g.
8. The method according to claim 6, wherein the is administered in a dose of about 0.25 to about 2 µg/g.
9. The method according to claim 6, wherein the polypeptide is administered in a dose of about 1 µg/g.
10. The method according to claim 6, wherein the polypeptide is administered once daily.
11. The method according to claim 6, wherein of the polypeptide is administered about 2 times per day.
12. A method of lowering blood glucose level in a subject in need thereof, the method comprising administering to the subject an effective amount of a polypeptide, wherein the amino acid sequence of the polypeptide is:

(SEQ ID NO. 3)
GEVSADQVATVMWDYFSQLSNNAKEAVEHLQKSELTQQLNALFQDKLGE

VNTYAGDLQKKLVPFATELHERLAKDSEKLKEEIGKELEELRARLLPHA

NEVSQKIGDNLRELQQRLEPYADQLRTQVNTQAEQLRRQLTPYAQRMER

VLRENADSLQASLRPHADELKAKIDQNVEELKGRLTPYADEFKVKIDQT

VEELRRSLAPYAQDTQEKLNHQLEGLTFQMKKNAEEELKARISASAEELR

QRLAPLAEDVRGNLRGNTEGLQKSLAELGGHLDQQVEEFRRRVEPYGEN

FNKALVQQMEQLRQKLGPHAGDVEGHLSFLEKDLRDKVNSFFSTFKEKE

SQDKTLSLPELEQQQEQQQEQQQEQVQMLAPLES.

13. The method of claim 12, wherein the subject is a human.
14. The method according to claim 13, wherein the polypeptide is glycosylated.
15. The method according to claim 13, wherein the polypeptide is unglycosylated.
16. The method according to claim 15, wherein the polypeptide is administered systemically.
17. The method according to claim 16, wherein the systemic administration of the polypeptide is selected from the group consisting of oral, subcutaneous, intravenous, intramuscular, and intraperitoneal administration.
18. The method according to claim 17, wherein the polypeptide is administered in a dose of about 1 to about 10 µg/g.
19. The method according to claim 17, wherein the polypeptide is administered in a dose of about 0.25 to about 2 µg/g.
20. The method according to claim 17, wherein the polypeptide is administered in a dose of about 1 µg/g.
21. The method according to claim 17, wherein the polypeptide is administered once daily.
22. The method according to claim 17, wherein the polypeptide is administered about 2 times per day.

\* \* \* \* \*

UNITED STATES PATENT AND TRADEMARK OFFICE
CERTIFICATE OF CORRECTION

PATENT NO. : 9,051,394 B2
APPLICATION NO. : 13/980749
DATED : June 9, 2015
INVENTOR(S) : Patrick Tso et al.

Page 1 of 1

It is certified that error appears in the above-identified patent and that said Letters Patent is hereby corrected as shown below:

In the Specification

Column 1, after the priority information, please insert the following paragraph:
--FEDERALLY SPONSORED RESEARCH OR DEVELOPMENT
This invention was made with government support under DK056863 and DK076928 awarded by National Institutes of Health. The government has certain rights in the invention.--

Signed and Sealed this
Seventeenth Day of March, 2020

Andrei Iancu
*Director of the United States Patent and Trademark Office*